(12) United States Patent
Levin

(10) Patent No.: US 6,562,035 B1
(45) Date of Patent: May 13, 2003

(54) INSULATED SURGICAL SCISSORS INCLUDING CAUTERIZING TIP

(76) Inventor: John M. Levin, 819 Chauncey Rd., Narberth, PA (US) 19072

( * ) Notice: Subject to any disclaimer, the term of this patent is extended or adjusted under 35 U.S.C. 154(b) by 0 days.

(21) Appl. No.: 09/837,903

(22) Filed: Apr. 19, 2001

(51) Int. Cl.$^7$ ................................................ A61B 18/18
(52) U.S. Cl. .............................................. 606/45; 49/50
(58) Field of Search ............................. 606/41, 45, 46, 606/48–52, 170

(56) References Cited

U.S. PATENT DOCUMENTS

| | | |
|---|---|---|
| 1,813,902 A | 7/1931 | Bovie |
| 4,128,099 A | 12/1978 | Bauer |
| 4,375,218 A | 3/1983 | DiGeronimo |
| 4,499,899 A | 2/1985 | Lyons, III |
| 4,671,274 A | 6/1987 | Sorochenk |
| 4,890,610 A | 1/1990 | Kirwan, Sr. et al. |
| 5,026,370 A | 6/1991 | Lottick |
| 5,116,332 A | 5/1992 | Lottick |
| 5,147,356 A | 9/1992 | Bhatta |
| 5,147,357 A | 9/1992 | Rose et al. |
| 5,171,256 A | 12/1992 | Smith et al. |
| 5,217,460 A | 6/1993 | Knoepfler |
| 5,234,453 A | 8/1993 | Smith et al. |
| 5,295,990 A | 3/1994 | Levin |
| 5,342,381 A | 8/1994 | Tidemand |
| 5,352,222 A | 10/1994 | Rydell |
| 5,356,408 A | 10/1994 | Rydell |
| 5,373,854 A | 12/1994 | Kolozsi |
| 5,540,685 A * | 7/1996 | Parins et al. ................... 606/48 |
| 5,573,534 A | 11/1996 | Stone |
| 5,766,166 A * | 6/1998 | Hooven ......................... 606/45 |
| 5,827,281 A * | 10/1998 | Levin ........................... 606/170 |
| 5,860,975 A * | 1/1999 | Goble et al. ................... 606/41 |
| 5,921,984 A * | 7/1999 | Sutcu et al. .................... 606/46 |

FOREIGN PATENT DOCUMENTS

| | | |
|---|---|---|
| EP | 0 593 929 | 4/1994 |
| FR | 2 355 521 | 1/1978 |

* cited by examiner

Primary Examiner—Michael Peffley
(74) Attorney, Agent, or Firm—Caesar, Rivise, Bernstein, Cohen & Pokotilow, Ltd.

(57) ABSTRACT

An insulated surgical scissors including a cauterizing tip that permits a surgeon the ability to mechanically cut tissue that is purchased between the cutting blades of the scissors and to apply a cauterization current to a precise portion of the seized tissue, thereby minimizing inadvertent burning of surrounding tissue. Both monopolar and bipolar configurations of the insulated surgical scissors are provided.

14 Claims, 5 Drawing Sheets

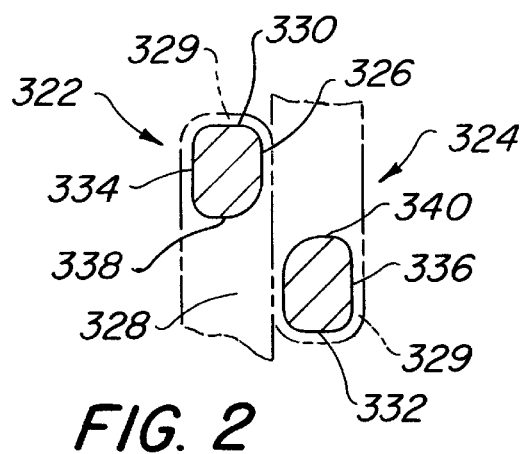
FIG. 2
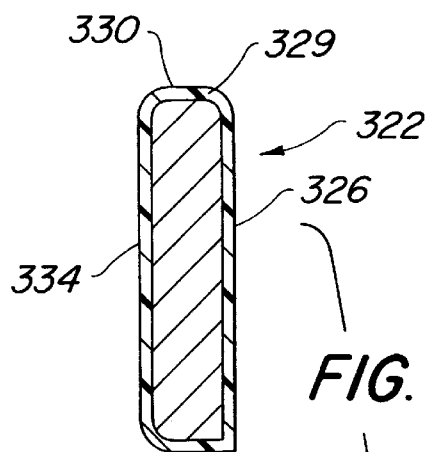
FIG. 3
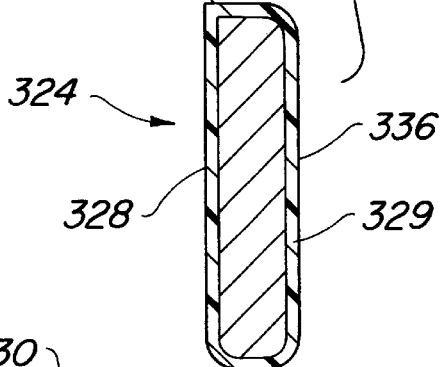
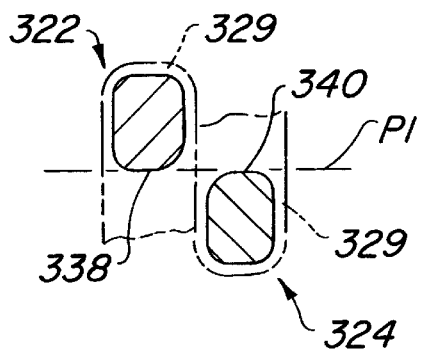
FIG. 5
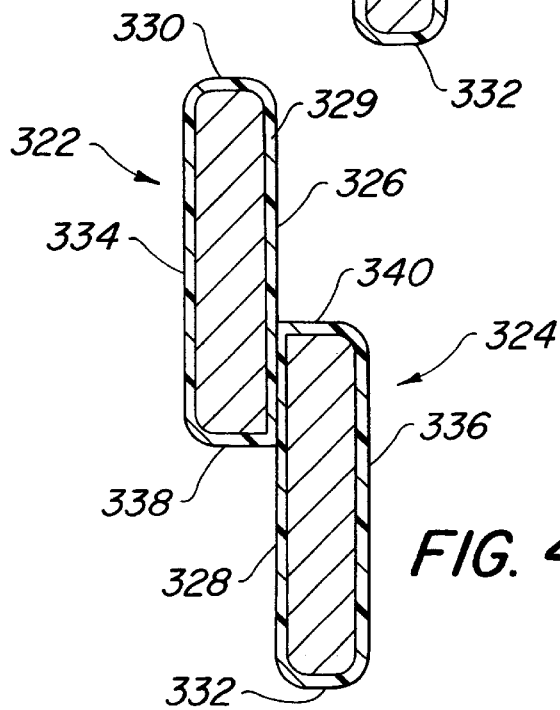
FIG. 4

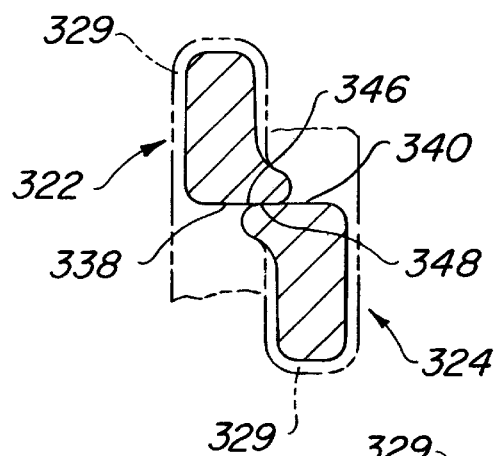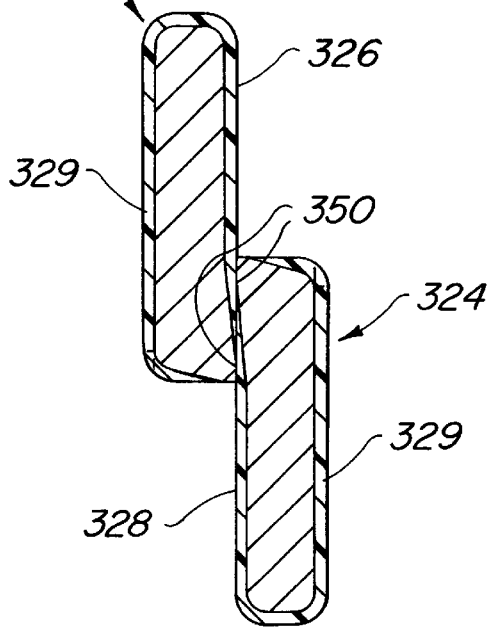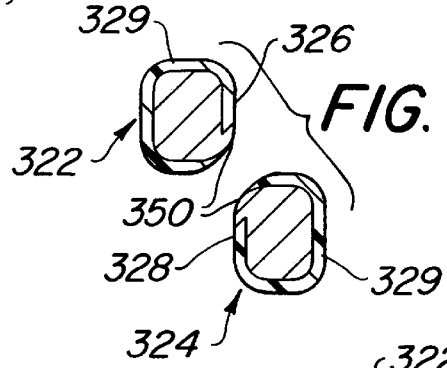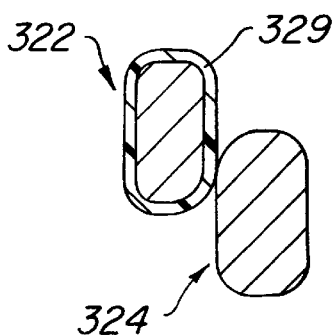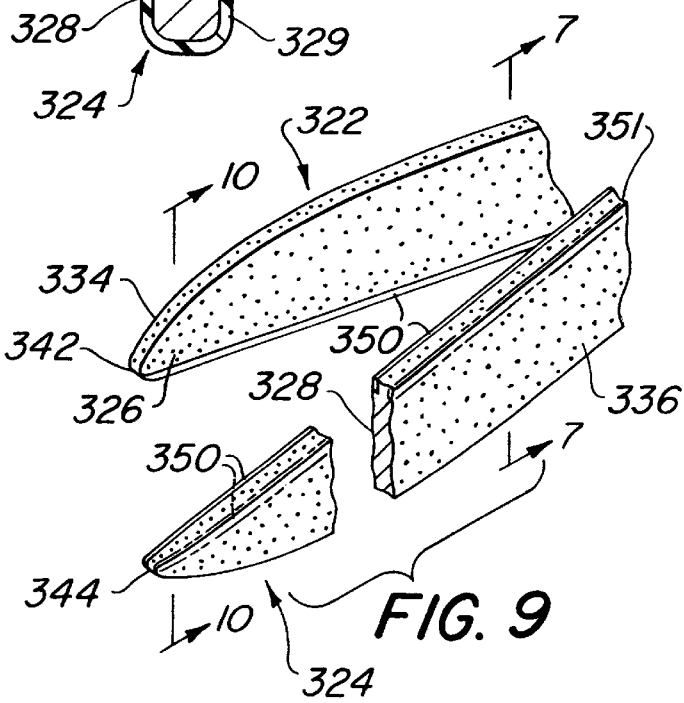

FIG. 15
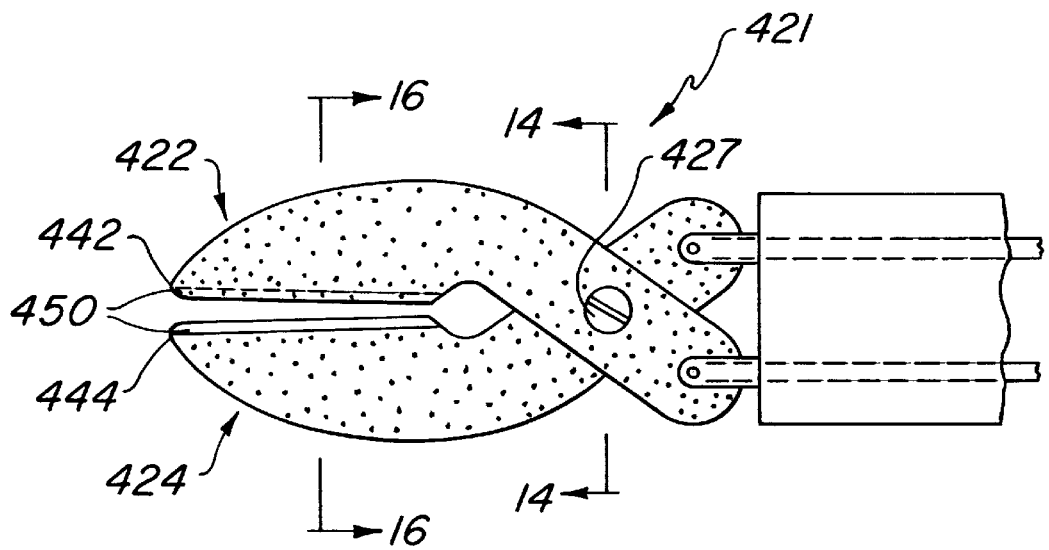
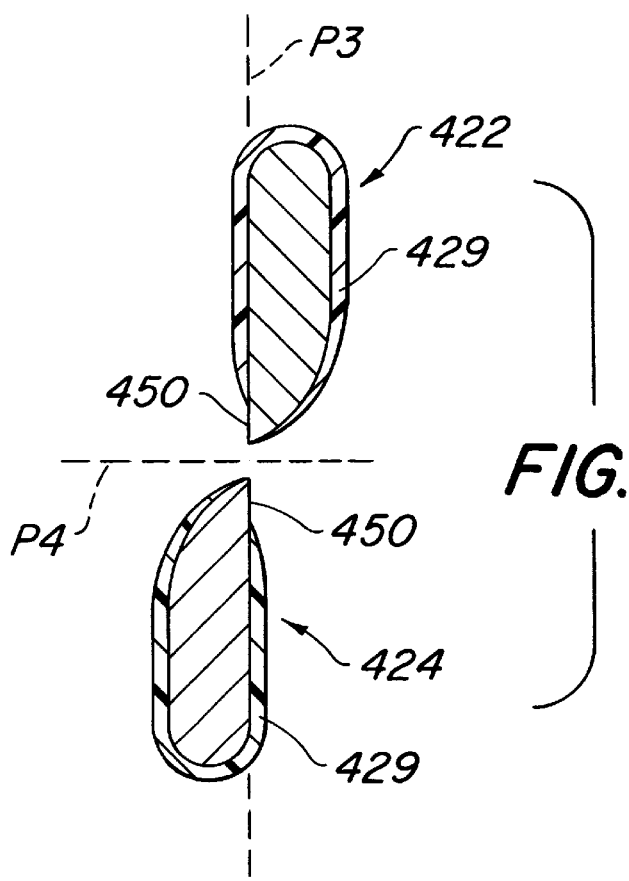
FIG. 16

INSULATED SURGICAL SCISSORS INCLUDING CAUTERIZING TIP

FIELD OF THE INVENTION

This invention relates generally to the field of insulated surgical scissors and more particularly to both monopolar and bipolar scissors constructions that can be specifically adapted for use in laparoscopic, endoscopic and open surgery surgical procedures.

BACKGROUND OF THE INVENTION

Insulated forceps, biopsy devices and clamping devices having the capability of providing a coagulating function are known in the art. These devices provide a significantly different function and have different design considerations than insulated scissors of the type forming the subject matter of this invention.

For example, forceps are principally designed to grip and hold tissue and/or organs during a surgical procedure; not to sever tissue between cooperation cutting edges of blades that move past each other to provide the severing operation, as in the operation of scissors within the scope of this invention. This prior art directed to the construction and design of insulated, cauterizing forceps are not relevant to the insulated scissors of this invention. Representative surgical forceps are disclosed in U.S. Pat. No. 5,217,460 (Knoepfler); U.S. Pat. No. 5,116,332 (Lottick), U.S. Pat. No. 5,026,370 (Lottick); U.S. Pat. No. 4,671,274 (Sorochenko); U.S. Pat. No. 4,890,610 (Kirwan, Sr., et al.); U.S. Pat. No. 5,147,357 (Rose, et al.); U.S. Pat. No. 4,375,218 (DiGeronimo); U.S. Pat. No. 4,128,099 (Bauer); U.S. Pat. No. 1,813,902 (Bovie).

Biopsy instruments also provide a significantly different function, and have different design considerations than the insulated scissors of the type forming the subject matter of this invention. In particular, biopsy devices are designed to separate and remove (often within a closed compartment of the device) portions of body tissue, growths, etc. from a patient's body. In distinction to biopsy devices, the function of insulated scissors within the scope of this invention is to sever tissue or other body parts between relatively movable cutting blades, without necessarily having any separate capability to confine the severed tissue and/or body part and remove it from the patient's body. Thus, prior art directed to the construction and design of insulated, cauterizing biopsy devices are not relevant to the insulated scissors of this invention. Representative surgical biopsy devices are disclosed in the following publications: U.S. Pat. No. 5,373,854 (Kolozsi); U.S. Pat. No. 5,295,990 (Levin); and European Patent Application 0 593 929 A1 (United States Surgical Corporation).

A wide variety of surgical "cut and coagulation" scissors also are known in the prior art, as exemplified by U.S. Pat. No. 5,573,534 (Stone); U.S. Pat. No. 5,356,408 (Rydell); U.S. Pat. No. 5,352,222 (Rydell); U.S. Pat. No. 5,342,381 (Tidemand); U.S. Pat. No. 5,234,453 (Smith, et al.); U.S. Pat. No. 5,171,256 (Smith, et al.); U.S. Pat. No. 5,147,356 (Bhatta); U.S. Pat. No. 4,499,899 (Lyons, III). As noted above, surgical scissors are utilized for purposes that are significantly different from the previously identified coagulating biopsy or forceps devices.

John M. Levin, the inventor of the subject matter described and claimed herein also is the inventor of the insulated cut/coagulate surgical scissors disclosed in U.S. Pat. No. 5,827,281 (Levin), whose entire disclosure is incorporated by reference herein. The scissors disclosed in the '281 Levin patent have a monopolar or a bipolar construction, which can be used during laparoscopic, endoscopic and open surgery for mechanically/electrically cutting and coagulating tissue. The jaws of these surgical scissors are covered in their entirety by insulation except for selected portions along the cutting edges and the tips to minimize undesirable burning/cutting of surrounding tissue. The present invention relates to modified forms of the insulated scissors described in the Levin '281 patent.

The apparatus disclosed by Stone is a bipolar electro surgical instrument comprising jaws fabricated from an insulating material having conductive pathways. These conductive pathways permit sparking between the pathways when the jaw members are open. As the jaw members are brought together, the insulating jaw member material blocks the electrical path between the conductive pathways to terminate electrical treatment of tissue trapped between the jaw members.

The apparatus disclosed by the Rydell patents are surgical scissors with a bipolar coagulation feature. The scissors disclosed therein comprise a pair of opposed blade members pivotally joined to one another through an insulated bushing member. Each of the blade members comprises a blade support and a blade, each fabricated from a metal but yet separated by a dielectric bonding agent. Cutting is performed at the blade level and cauterization occurs through the passage of electricity from one blade support and through the tissue to the other blade support. In other words, the passage of electricity is not through either of the blades that cut the tissue. Instead, electricity flows from one blade support (above and below the cut made by the blades), through the tissue trapped between the blade members, and into the other blade support.

The apparatus disclosed by Tidemand is a combination bipolar scissors and forceps instrument. The scissors disclosed therein comprises a pair of interfacing blade surfaces. Each of the interfacing blade surfaces comprises an insulative ceramic layer of approximately 0.020 inches. During scissoring action, a gap of approximately 0.040 inches is created between the interfacing scissors surfaces. Tidemand states that this gap is small enough to allow an RF current applied to the interfacing blade members to "bridge" the gap and effect a cauterization on any tissue trapped between the blades.

The apparatus disclosed by Smith, et al. ('453) is a disposable laparoscopic scissors utilizing cobalt-based alloy scissor elements that can be double acting (two movable jaws) or single acting (a single movable jaw in combination with a fixed jaw) and includes a plastic shrink wrap applied to the aluminum tube.

The apparatus disclosed by Smith, et al. ('256) is also a disposable laparoscopic scissors that can be double acting or single acting and includes plastic shrink wrap applied to the aluminum tube and portions of the actuation means at the working end of the instrument to electrically insulate the instrument.

The apparatus disclosed by Bhatta is a scissors-like surgical instrument with a cutting and cauterizing heat source such as a hot wire element or a laser transmission fiber carried in at least one of the jaws members.

The apparatus disclosed by Lyons, III is a rotary cutting scissors for microsurgery that includes an internal fiber light source for illuminating the surgical area.

Even in view of the above-described prior art disclosures, a need still exists for improved surgical scissors construction that allows the surgeon to cut tissue and to immediately coagulate the opening created by the cut while at the same time minimizing or eliminating any burning of surrounding tissue. In addition, it is important to be able to restrict the electric current flow through the patient's tissue when using such an apparatus.

SUMMARY OF THE INVENTION

An apparatus for cutting and cauterizing tissue during surgery while minimizing electrical and thermal contact of the apparatus with surrounding tissue. The apparatus comprises: a pair of opposing electrically conductive cutting blades pivotally connected to allow for shearing action of any tissue confined between opposed cutting edges of the cutting blades wherein the blades have blunted tips and wherein the pair of opposing cutting blades are entirely covered with an electrically and thermally insulative material except at the blunted tips; and a power source coupled to at least one of said pair of opposing cutting blades for electrically and thermally energizing at least one of said pair of blades.

An apparatus for cutting and cauterizing tissue during surgery while minimizing electrical and thermal contact of the apparatus with surrounding tissue. The apparatus comprises: a pair of opposing electrically conductive cutting blades pivotally connected to allow for shearing action of any tissue confined between opposed cutting edges of the cutting blades wherein the is entirely covered with an electrically and thermally insulative material including its blunted tip and the other one of the pair of opposing cutting blades is entirely covered with an electrically and thermally insulative material except at its corresponding blunted tip; and a power source coupled to at least one of the pair of opposing cutting blades for electrically and thermally energizing at least one of the pair of blades.

An apparatus for cutting and cauterizing tissue during surgery while minimizing electrical and thermal contact of the apparatus with surrounding tissue. The apparatus comprises: a pair of opposing electrically conductive cutting blades pivotally connected to allow for shearing action of any tissue confined between opposed cutting edges of the cutting blades wherein the blades have blunted tips and wherein the pair of opposing cutting blades is entirely covered with an electrically and thermally insulative material except on confronting surfaces at the blunted tips; a power source having a power side that is electrically coupled to one of the pair of opposing cutting blades and having a ground side that is electrically coupled to the other one of the pair of opposing cutting blades for generating a cauterization current that flows through tissue trapped between the confronting surfaces at the blunted tips.

DESCRIPTION OF THE DRAWINGS

Many of the attendant advantages of this invention will be readily appreciated as the same becomes better understood by reference to the following detailed description when considered in connection with the accompanying drawings wherein:

FIG. 1A is an enlarged view of the working end of the insulated surgical scissors of FIG. 1;

FIG. 2 is an enlarged, cross-sectional view of the insulated surgical scissors taken along line 2—2 in FIG. 1A, but with the blades in a partially-closed position;

FIG. 3 is an enlarged, cross-sectional view of the insulated surgical scissors taken along line 3—3 in FIG. 1A;

FIG. 4 is an enlarged, cross-sectional view of the insulated surgical scissors taken along 4—4 in FIG. 1A, but with the blades in a partially-closed position;

FIG. 5 is an enlarged, cross-sectional view of the working end of a second embodiment of the monopolar insulated surgical scissors, taken along a line corresponding to the location of line 2—2 in FIG. 1A, whereby the blade tips do not pass when the blades are in a closed position;

FIG. 6 is an enlarged, cross-sectional view of the working end of a third embodiment of the monopolar insulated surgical scissors, taken along a line corresponding to the location of line 2—2 in FIG. 1A, whereby the blade tips abut each other in the closed position;

FIG. 7 is an enlarged, cross-sectional view, taken along line 7—7 in FIG. 9, of the working end of a fourth embodiment of the monopolar insulated surgical scissors whereby a sliver on the inside surface of each blade is exposed;

FIG. 8 is an enlarged, cross-sectional view of the working end of a fifth embodiment of the monopolar insulated surgical scissors, taken along a line corresponding to the location of line 2—2 in FIG. 1A, whereby only one of the blades has an exposed tip;

FIG. 9 is an enlarged, partial isometric view of the working end of the fourth embodiment of the monopolar insulated surgical scissors showing the position of an exposed sliver on the inside surface of the upper blade and an exposed sliver on the inside surface of the lower blade; alternatively, these slivers could be on the outside surface of the blades, as shown in phantom in the lower blade;

FIG. 10 is an enlarged, cross-sectional view of the working end of the embodiment of FIG. 9 taken along line 10—10 in FIG. 9;

FIG. 15 is an enlarged, side view of the working end of a bipolar configuration of the insulated surgical scissors; and FIG. 16 is an enlarged, cross-sectional view of the of the bipolar insulated surgical scissors taken along line 16—16 in FIG. 15.

DESCRIPTION OF THE PREFERRED EMBODIMENTS OF THE INVENTION

Figure 1:
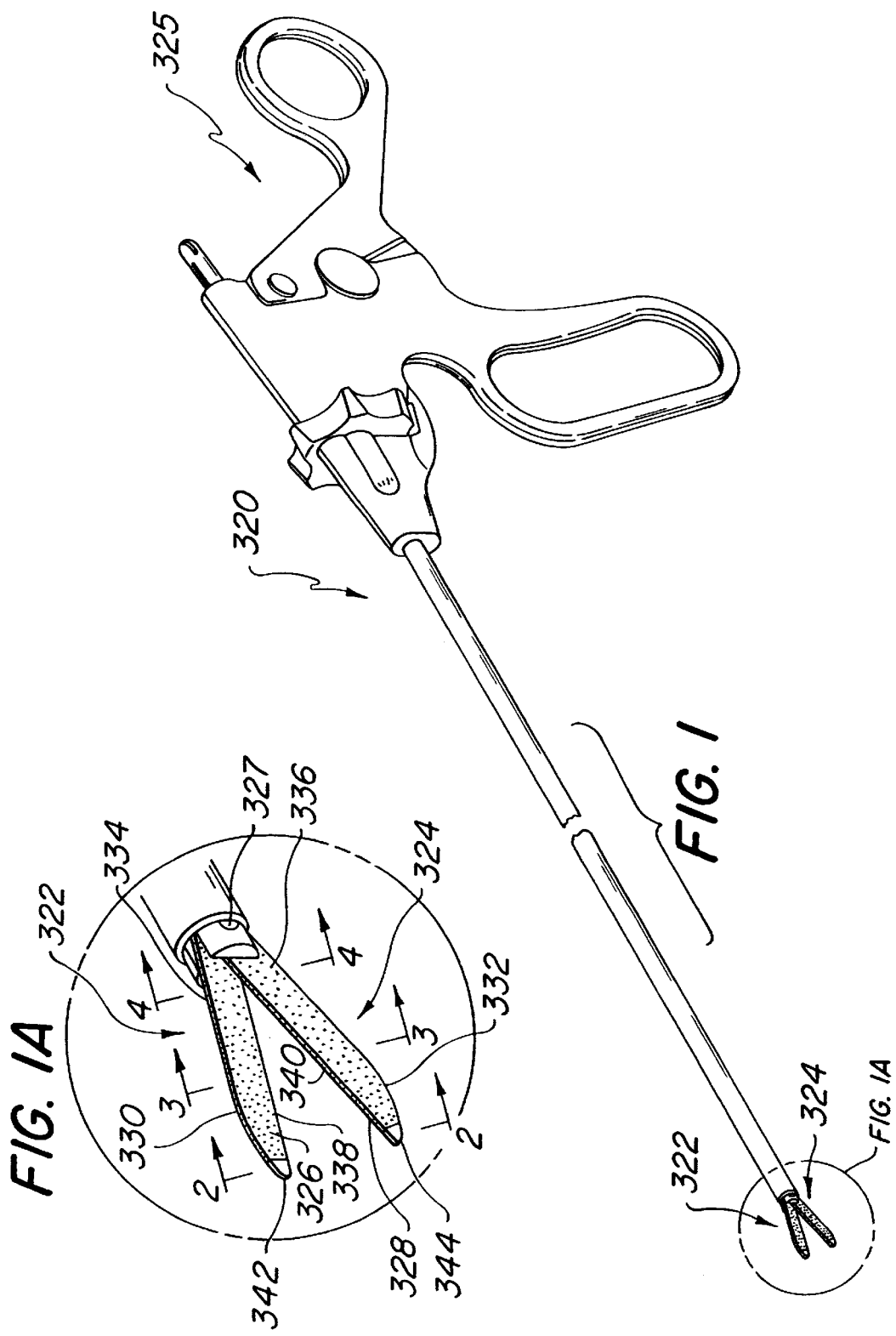
FIG. 1 is a fragmentary, isometric view of a monopolar insulated surgical scissors of the present invention.

Referring now in greater detail to the various figures of the drawing wherein like reference characters refer to like parts, an insulated monopolar surgical scissors constructed in accordance with the present invention is shown generally at 320 in FIG. 1. The insulated monopolar surgical scissors 320 comprises a pair of opposed cutting blades 322 and 324.

The insulated surgical scissors 320 is electrically energized for accomplishing the coagulation of blood vessels and/or other tissue that have been severed during the cutting operation. In particular, the scissors 320 comprises a monopolar configuration, i.e., electrical energy is delivered from a power source (not shown) via a first electrical conductor (also not shown) to the scissors blades 322 and 324 (each comprising a metal such as stainless steel for conducting electricity), with both blades 322 and 324 being at the same voltage. The return for the electrical energy from the scissors 320 is through the patient (not shown) to a large surface (e.g., a conducting plate, not shown) located underneath the patient and then back to the power source via a second electrical conductor (not shown), as is well-known in the art, such as that shown in FIG. 1 of U.S. Pat. No. 5,827,281 (Levin), which has already been incorporated by reference in its entirety. In accordance with FIG. 1 of the '281 Levin patent, the first electrical conductor enters the insulated surgical scissors 320 at the proximal end, i.e., adjacent an actuation/handle portion 325 of the scissors 320. The first conductor is fed through the insulated surgical scissors 320 where the first conductor passes the electrical energy to the blades 322 and 324 via a conductive pivot fastener 327.

In one preferred embodiment of the invention, this pair of opposed cutting blades 322 and 324 are completely insulated, except for one or more surfaces at the distal end of the scissors 320, as will be described in greater detail hereinafter. However, in all embodiments the opposed cutting blades 322 and 324 of the scissors 320 include rounded or blunted distal edges to preclude the cutting of tissue trapped between the blades at the distal end. The complete insulation may be accomplished by an electrically and thermally insulative layer 329 (e.g., using a ceramic material or readily available liquid electrical insulation material) applied to each blade 322 and 324 while masking the one or more surfaces to create the selected uninsulated (i.e., conductive) surfaces. Alternatively, instead of masking these surfaces, the insulative layer 329 can be applied to the blades 322/324 in their entirety and then removed, e.g., by filing, grinding, etc., from the distal end regions that are intended to be conductive for providing the electrical cutting or cautery operation.

In accordance with the broadest aspects of the invention, any or all surfaces at the distal end of one or both of the blades 322 and 324 can be made conductive to provide either an electrical cutting or cauterizing operation. To further explain, as shown in FIG. 1A, the inner side surface (326/328), the upper edge surface (330/332), the outer side surface (334/336), the lower edge surface (338/340), and the distal end surface (342/344) in the distal region of one or both blades 322 and 324 can be conductive to provide an electrical cutting or cauterizing operation. To achieve mechanical cutting of the tissue between the blades 322 and 324, the blades 322 and 324 are closed by the surgeon using the handle portion 325 in a conventional manner. During closure, the exposed tips of the blades 322 and 324 approach each other (FIG. 2-partial closure) and then overlap during full closure (not shown) so that inside surfaces 326 and 328 are adjacent each other. FIGS. 3–4 depict how the insulated proximal or back portion of the blades 322 and 324 approach each other and then overlap during closure.

It should be understood that, alternatively, only one or more of such surfaces (i.e., the inner side surfaces 326/328, the upper edge surfaces 330/332, the outer side surfaces 334/336, the lower edge surfaces 338/340 and the distal end surfaces 342/344, collectively referred to as the "candidate" surfaces) can be selectively conductive to provide a cauterizing operation.

When the inwardly facing surfaces (326/328) at the distal ends of the cutting blades 322/324 are electrically conductive to provide an electrical cutting or cauterizing operation, they are operated by either purchasing the tissue to be cut or cauterized between them or the cutting or cauterizing operation is carried out with the scissors 320 in an open condition.

It is within the scope of this invention to make any amount or all of the outer circumference of the distal tip portion, of either or both blades 322/324, electrically conductive. However, it is important that confronting surfaces of the blades at the distal end be configured to be blunt, so as not to mechanically cut tissue that is positioned between the blades 322/324 at the distal ends thereof.

Figure 11:
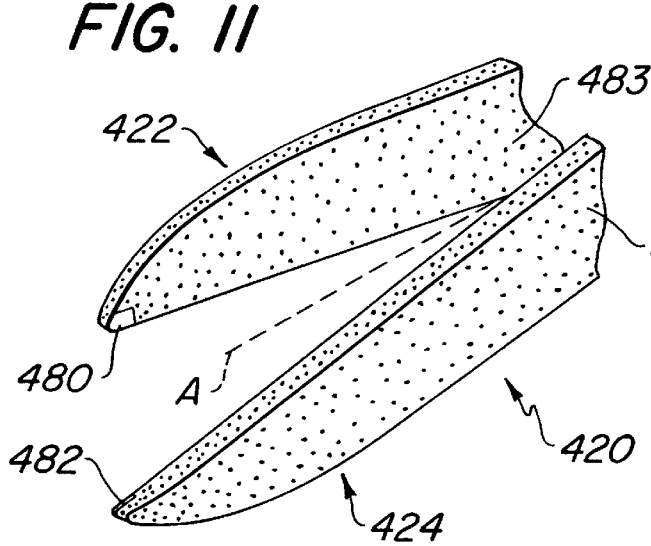
FIG. 11 is enlarged, partial isometric view of the working end of either a monopolar or a bipolar surgical scissors having the extreme tip on the inside surfaces of the blades exposed.

In the preferred embodiment of the invention 320 the conductive region of the tip is located in a region which is no more than 5 millimeters from the distal edge of the blades 322/324 (i.e., from the distal end surfaces 342/344 back towards the conductive pivot fastener 327), and more preferably is in the forward, or most distal 1–3 millimeters of the blades 322/324 (see FIG. 11).

FIG. 5 depicts a similar type of monopolar scissors as shown in FIGS. 1–4 but in the embodiment of FIG. 5, the uninsulated tip regions do not pass each other when the scissors 320 is in its fully-closed position. Instead, the lower edge surface 338 of blade 322 and the lower edge surface 340 of blade 324 lie along the same plane P1 when the scissors are in a fully-closed position. As a result, the uninsulated tip regions act as a "clamp" for purchasing tissue and then, when electrically activated, the uninsulated tip region can either electrically cut or coagulate tissue. To prevent the uninsulated tip regions from passing each other, any number of well-known mechanisms, or their equivalents, can be used such as having the handle portion 325 comprise a stop to prevent the uninsulated tip regions from passing each other; or by configuring the proximal or back portion of each blade 322/324 to interact with each other to prevent the uninsulated tip regions from passing each other, or by configuring the tip regions so that they do not pass each other.

FIG. 6 depicts another monopolar scissors wherein the uninsulated tip region of each blade 322 and 324 comprises abutting, or engaging, surfaces 346 and 348, respectively. Thus, the lower edge surface 338 of blade 322 and the lower edge surface 340 of blade 324 comprise abutting surfaces 346 and 348, respectively, to prevent the overlapping of the blades 322 and 324 at the tips thereof.

FIGS. 7 and 9–10 depict an alternative monopolar embodiment of the invention in which a very small sliver 350, e.g., on the order of a millimeter, of conductive material extends along either the entire length or a fraction of the length of the inside surfaces 326 and 328 of the blades 322 and 324, respectively, or of the outside surfaces 334 and 336 of the blades 322 and 324, respectively. Alternatively, the sliver 350 can be on the inside surface or the outside surface of only one of the blades 322 or 324. When the sliver 350 extends only over a fraction of the length of blade 322 and/or blade 324, it preferably extends over a distal region thereof adjacent the conductive tip but does not include the distal end surfaces 342/344.

As stated above, the sliver 350 can be on both the inside surfaces (326 and 328) and/or the outside surfaces (334 and 336) of one or both blades 322 and 324. Preferably, however, the sliver 350 is included on the inner confronting surfaces (i.e., 326 and 328) of the blades 322 and 324 that are intended to provide a mechanical cutting operation.

It also should be understood that injury tends to occur when conductive surfaces of the scissors 320 that cannot be viewed by the surgeon inadvertently come in contact with undesired regions in the vicinity of the surgical sight. However, when a conductive sliver 350 is provided along an outer edge (as shown in phantom by the reference number 351 in FIG. 9) of one or both of the blades 322/324, they are generally oriented so that the surgeon can see at least one of them while providing a cutting or cauterizing operation, thereby minimizing the likelihood that an inadvertent injury will be caused to the patient.

FIG. 8 depicts another embodiment of the monopolar scissors wherein one of the blades, (e.g., blade 322) is covered in its entirety with the insulative layer 329 whereas the tip region of the other blade 324 comprises the selective uninsulated surfaces. Although all of the candidate surfaces at the tip of blade 324 are illustrated as being conductive, uninsulated surfaces, it is within the scope of this invention to make one or more, but less than all, of such candidate surfaces conductive.

In summary, the distal tip section of blade 322 and/or 324 is provided with one or more conductive surfaces (i.e., candidate surfaces) to provide a cauterizing or cutting operation, and the variations of surfaces which can be made electrically conductive are the same as described above in connection with the earlier embodiments of this invention.

Figure 12:
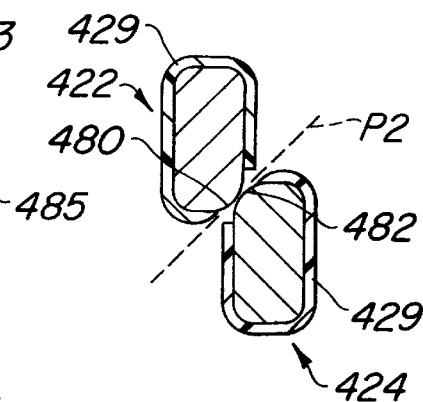
FIG. 12 is an enlarged, cross-sectional view taken along line 12—12 in FIG. 11 showing the blade tips overlapping and the scissors in a closed position.

The manner in which the blades 322 and 324 are operated by the surgeon is through the actuation of the handle portion 325 (FIG. 1). It should be understood that scope of the present invention is not limited to employing any specific actuation/handle portion, and that any conventional actuation/handle portion for effecting relative movement of blades at the distal end of a surgical device (both laparoscopic and non-laparoscopic) can be used with the present invention, such as that set forth in U.S. Pat. No. 5,234,453 (Smith et al.), the entire disclosure of which is incorporated by reference herein. Therefore, a detailed explanation of the actuation/handle portion 325 is omitted from this application. There is shown at 420 in FIGS. 11–12 an insulated surgical scissors having a pair of jaws 422 and 424 electrically coupled in a bipolar configuration. A bipolar configuration means that each blade forms an electrode with one blade being at the voltage of a power source (not shown) while the other blade is electrically coupled to the ground side of the power source. FIG. 8 of U.S. Pat. No. 5,827,281 (Levin), whose entire disclosure has already been incorporated by reference herein, depicts the bipolar electrical activation of the working end. Hence, electrical energy flow is now confined to the following path: power source to one blade 424, (which comprises a metal such as stainless steel for conducting electricity) via a first electrical conductor (not shown), through the tissue (not shown) wedged between the pair of blades 422/424, out into the other blade 422 (which comprises a metal such as stainless steel for conducting electricity) and then back to the power source via a second electrical conductor (not shown). As such, there is no conductive plate that the patient must lie on and there is no flow of current through the patient's body other than through the tissue between the blades.

Actuation of the bipolar jaws by a handle portion (not shown) of the insulated surgical scissors is the same or similar to the handle portion 325 described earlier with respect to the monopolar insulated surgical scissors 320, and, as a result, is not explained any further herein.

Like the monopolar insulated surgical scissors 320, the bipolar insulated surgical scissors is completely insulated (e.g., using a ceramic material or readily available liquid electrical insulation material), both electrically and thermally, on all of its exposed surfaces. As such, an insulative layer 429 covers almost the entire scissors 420. The only portions of the bipolar insulated surgical scissors 420 that are not electrically and thermally insulated are confronting inner surfaces of the blades 422 and 424, discussed below.

In a bipolar configuration, although electrical energy is easily conducted through both blades 422 and 424, there is no flow of electrical energy into, nor out of, any unexposed portion of the bipolar surgical scissors 420. It should be noted that the pivot point (not shown in FIG. 11) between the upper and lower blades 422 and 424 must be electrically and thermally insulated to ensure that there is no short that would cause the flow of electrical energy from the one blade (e.g., 424) to the other blade (e.g., 422) and thereby bypass the confronting inner surfaces of the blades 422 and 424.

Figure 14:
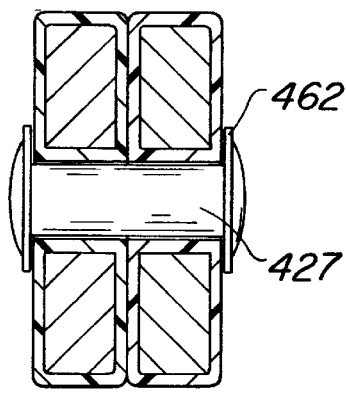
FIG. 14 is an enlarged, cross-sectional view of the connecting pivot fastener taken along line 14—14 in FIG. 15.

One way of providing this electrical/thermal insulation at the pivot point is to fully insulate the entire periphery of the blades 422/424 in the region of the pivot point, including the inner surface of the passage for receiving the pivot pin. Such an arrangement is illustrated in FIG. 14 and will be discussed in greater detail in connection with the bipolar scissors configuration of FIGS. 15–16.

Moreover, since the exit flow of electrical energy, in the bipolar configuration, is confined to the confronting inner surfaces of the jaws 422 and 424 of the scissors 420, the only portions of the scissors that conduct heat are these confronting inner surfaces. As such, any burning or smoking of tissue caused by the surgical scissors 420 being electrically active is restricted to tissue trapped between the confronting inner surfaces. Therefore, in the bipolar variants of this invention discussed below, the uninsulated conductive portions of the tip cannot include the entire exposed circumference since undesired shorting would occur. It is important that the cooperating conductive surfaces be "inner" conductive surfaces to avoid undesired arcing and burning of tissue.

In a first embodiment of this bipolar surgical scissors 420, all of the surfaces of the blades 422 and 424 are insulated, except for confronting inner surfaces 480 and 482 at the distal end of the blades 422 and 424, respectively. In this connection, the confronting inner surfaces 480 and 482 of the blades 422 and 424, respectively, preferably are configured with blunt and/or rounded surfaces to preclude the mechanical cutting of tissue disposed between them. As shown most clearly in FIG. 12, the tips of the blades 422 and 424 can be configured so that conductive surfaces 480 and 482 of adjacent tips engage the tissue (not shown) along a plane P2 obliquely oriented to the elongate axis, A, of the scissors 420 (FIG. 11).

It should be noted that with the entirety of the blades 422 and 424 being insulated except for the confronting inner surfaces 480 and 482, there is no concern for any shorting, i.e., electrical energy bypassing flow through the confronting inner surfaces 480 and 482, if the back portion 483 and 485, respectively, of the blades 422 and 424 overlap before the confronting inner surfaces 480 and 482 during closure.

Figure 13:
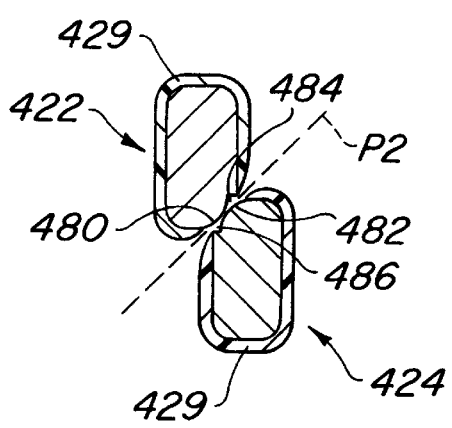
FIG. 13 is an enlarged, cross-sectional view of the blades in FIG. 11 including a set-back feature at the extreme tip of the blades showing the blades in a closed position.

If desired, the confronting inner conductive surfaces 480 and 482 at the distal end of the blades 422 and 424 in the bipolar version of this invention can either be in the form of raised inner projections (not shown) or recessed grooves (FIG. 13). If these regions are in the form of raised projections, the mechanical cutting action of the blades 422 and 424 will take place until the raised projections engage each other. In particular, FIG. 13 depicts an embodiment similar to the embodiment of FIG. 11 but which includes uninsulated recessed grooves 484 and 486 (also known as "set-backs") in the distal tip regions. Thus, during closure, the recessed grooves 484 and 486 form a small cavity for capturing tissue therein and wherein this tissue is exposed to the confronting inner conductive surfaces 480 and 482.

FIGS. 15–16 depict an additional embodiment 421 of this bipolar surgical scissors invention whereby the confronting inner surfaces engage the tissue along a plane P3 (FIG. 16) that is substantially perpendicular to the pivot axis (schematically depicted as "PA" in FIG. 16) of the scissors 421. In particular, a slight sliver 450 of conductive material can be provided along the inside cutting edges of the scissors 421. In this embodiment, the scissors 421 preferably is designed so that the entire length of the slivers 450 of both cutting blades 422 and 424 tend to engage each other at the same time, to thereby avoid undesired arcing. In this embodiment of the invention, the sliver 450 can extend to the distal tip of each blade 422 and 424, or can actually terminate short of the end surfaces 442 and 444. In this latter embodiment, the tips of the blades 422/424 can be completely insulated with the entire cautery or cutting operation taking place in the region where the conductive slivers 450 overlap.

In the additional embodiment 421, as shown most clearly in FIG. 15, the physical design of blades 422 and 424 permits the conductive slivers 450 to be brought together, whenever the surgical scissors are closed by the surgeon, such that the contact along the entire length of their corresponding cutting edges is simultaneous. In other words, each blade 422 and 424 is angled so that the front edge portions make contact at the same time that the rear edge portions make contact. Should the rear edge portions make contact before the front edge portions, an electrical short would occur, causing electrical energy to flow across the rear edge portions and bypass flowing through any tissue trapped between the front edge portions.

In a further embodiment of this bipolar surgical scissors invention is encompassed by the scope of this invention whereby the confronting inner surfaces engage the tissue along a plane that is substantially parallel to the pivot axis PA of the scissors 421. FIG. 15 of U.S. Pat. No. 5,827,281 (Levin) depicts such a construction.

It should be understood that it is also within the scope of that present invention that all of the bipolar embodiments discussed above could be designed with any one of the three tissue-engaging orientations, i.e., (1) engaging the tissue along a plane P2 obliquely oriented to the elongate axis, A, of the bipolar scissors 420; (2) engaging the tissue along a plane P3 that is substantially perpendicular to the pivot axis PA of the bipolar scissors 421; or (3) engaging the tissue along a plane that is substantially parallel to the pivot axis PA of the scissors 421.

The bipolar embodiments of the insulated scissors of this invention can be made by first completely insulating each of the blades 422 and 424, including the passage 462 (FIG. 14) that is required to receive a screw 427 for pivotally attaching the blades 422/424 together. The screw 427 is then positioned through the insulated passage 464. Thus, in this invention, it is not required that the screw 427 also be insulated, since the inner surface of the passage 464 surface is insulated.

It should be noted that in both the monopolar and bipolar scissors of this invention, the most desirable embodiments are those in which the exposed conductive areas are at the minimum required to provide the desired electrical cutting and/or cauterizing functions. In both the monopolar and bipolar scissors, minimizing the conductive area of the blades reduces the amount of current that is necessary to effect an electrical cutting or cauterizing operation. In the bipolar scissors of this invention, minimizing the conductive areas on the cutting blades provides the additional benefit of effectively controlling the flow of current through the tissue being electrically cut and/or cauterized.

Without further elaboration, the foregoing will so fully illustrate my invention that others may, by applying current or future knowledge, readily adopt the same for use under various conditions of service.

I claim:

1. An apparatus for cutting and cauterizing tissue during surgery while minimizing electrical and thermal contact of said apparatus with surrounding tissue, said apparatus comprising:

a pair of opposing electrically conductive cutting blades pivotally connected to allow for shearing action of any tissue confined between opposed cutting edges of said cutting blades, said blades having blunted tips, said pair of opposing cutting blades being entirely covered with an electrically and thermally insulative material except at said blunted tips;

wherein each of said cutting blades comprises an inner surface, an outer surface, an outer edge, the cutting edge and a distal edge surface, said blunted tip comprising said distal edge surface and forming a portion of said inner surface, said outer surface, said outer edge, and said cutting edge;

wherein each of said cutting blades is covered with an electrically and thermally insulative material except on said inner surface closely adjacent said cutting edge or except on said outer surface closely adjacent said cutting edge; and a power source coupled to at least one of said pair of opposing cutting blades for electrically and thermally energizing at least one of said pair of blades.

2. An apparatus for cutting and cauterizing tissue during surgery while minimizing electrical and thermal contact of said apparatus with surrounding tissue, said apparatus comprising:

a pair of opposing electrically conductive cutting blades pivotally connected to allow for shearing action of any tissue confined between opposed cutting edges of said cutting blades, said blades having blunted tips, said pair of opposing cutting blades being entirely covered with an electrically and thermally insulative material except on confronting surfaces at said blunted tips;

a power source having a power side that is electrically coupled to one of said pair of opposing cutting blades and having a ground side that is electrically coupled to the other one of said pair of opposing cutting blades for generating a cauterization current that flows through tissue trapped between said confronting surfaces at said blunted tips; and wherein each of said confronting surfaces comprises a set back, said set back forming a cavity for facilitating the capture of tissue between said cutting blades.

3. An apparatus for cutting and cauterizing tissue during surgery while minimizing electrical and thermal contact of said apparatus with surrounding tissue, said apparatus comprising:

a pair of opposing electrically conductive cutting blades pivotally connected to allow for shearing action of any tissue confined between opposed cutting edges of said cutting blades, said blades having blunted tips, one of said pair of opposing cutting blades being entirely covered with an electrically and thermally insulative material including its blunted tip and the other one of said pair of opposing cutting blades being entirely covered with an electrically and thermally insulative material except at its corresponding blunted tip; and a power source coupled to at least one of said pair of opposing cutting blades for electrically and thermally energizing at least one of said pair of blades.

4. The apparatus of claim 3 wherein said each of said cutting blades comprises an inner surface, an outer surface, an outer edge, the cutting edge and a distal edge surface, said blunted tip comprising said distal edge surface and forming a portion of said inner surface, said outer surface, said outer edge, and said cutting edge.

5. The apparatus of claim 4 wherein said portions of said inner surface, said outer surface, said outer edge and said cutting edge forming said corresponding blunted tip comprise lengths of less than 5 millimeters from said distal edge surface.

6. The apparatus of claim 3 wherein said portions of said inner surface, said outer surface, said outer edge and said cutting edge forming said corresponding blunted tip comprise lengths of between 1 and 3 millimeters from said distal edge surface.

7. The apparatus of claim 3 wherein said cutting blades comprise respective confronting surfaces, said apparatus including a closed condition wherein said confronting surfaces form overlapping surfaces when the tissue being cut is trapped therebetween.

8. The apparatus of claim 3 wherein said apparatus includes a closed condition whereby said respective cutting edges of said cutting blades lie in a common plane and do not pass each other.

9. The apparatus of claim 8 wherein each of said cutting blades comprises a stop surface along said cutting edge, said stop surfaces of said cutting blades contacting to prevent said cutting blades from passing each other during closure of said apparatus.

10. The apparatus of claim 4 wherein one of said cutting blades is covered with an electrically and thermally insulative material except on said inner surface closely adjacent said cutting edge.

11. The apparatus of claim 10 wherein one of said cutting blades is covered with an electrically and thermally insulative material except on said outer surface closely adjacent said cutting edge.

12. The apparatus of claim 4 wherein one of said cutting blades is covered with an electrically and thermally insulative material except on said outer surface closely adjacent said cutting edge.

13. The apparatus of claim 12 wherein one of said cutting blades is covered with an electrically and thermally insulative material except on said inner surface closely adjacent said cutting edge.

14. The apparatus of claim 3 wherein said power source is coupled to the other one of said pair of opposing cutting blades for electrically and thermally energizing the other one of said pair of blades.

* * * * *